United States Patent [19]

Nieusma

[11] Patent Number: 4,723,912
[45] Date of Patent: Feb. 9, 1988

[54] BARRIER FOR DENTAL AND MEDICAL INSTRUMENTS AND APPENDAGES

[76] Inventor: Dick Nieusma, 6839 S. Toledo #445, Tulsa, Okla. 74136

[21] Appl. No.: 863,351

[22] Filed: May 15, 1986

[51] Int. Cl.$^4$ .............................................. A61C 1/16
[52] U.S. Cl. .................................... 433/116; 433/229
[58] Field of Search ................... 433/77, 78, 79, 116, 433/229

[56] References Cited

U.S. PATENT DOCUMENTS

| | | | |
|---|---|---|---|
| 1,093,865 | 4/1914 | Lauderdale | 433/116 |
| 1,342,968 | 6/1920 | Moolten | 433/116 |
| 1,485,963 | 3/1924 | Curry | 433/116 |
| 1,539,253 | 5/1925 | Fuller | 433/116 |
| 3,528,720 | 9/1970 | Treace | 350/585 |
| 3,698,791 | 10/1972 | Walchle et al. | 350/61 |
| 4,266,935 | 5/1981 | Hoppe | 433/116 |

Primary Examiner—Robert P. Swiatek
Assistant Examiner—Adriene J. Lepiane
Attorney, Agent, or Firm—Price, Heneveld, Cooper, DeWitt & Litton

[57] ABSTRACT

A draping apparatus for covering dental and medical equipment and appendages extending therefrom such as water hoses, electric cords and the like. The apparatus includes an elongated sleeve and a ring-like element mounted on one end of the sleeve, the ring-like element being sufficiently rigid to define the periphery of the opening to the sleeve to permit an operator to grasp the same and pull the ring and sleeve over the instrument and appendages. Preferably, the apparatus is packaged in an enclosure attached to the ring-like element and adapted to be severed therefrom so that one end of the sleeve can be held in one hand of the operator and the other end to which the ring-like element is attached can be pulled over the instrument and its appendage.

18 Claims, 20 Drawing Figures

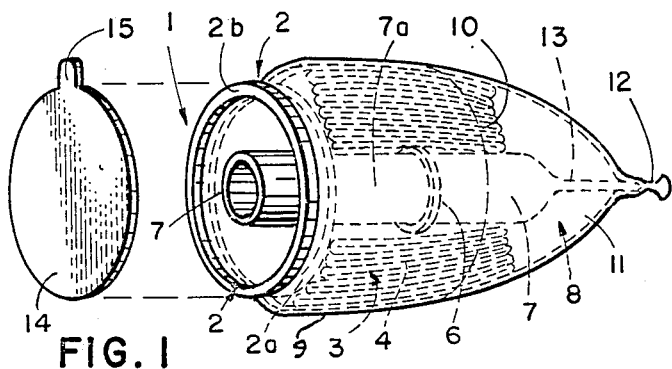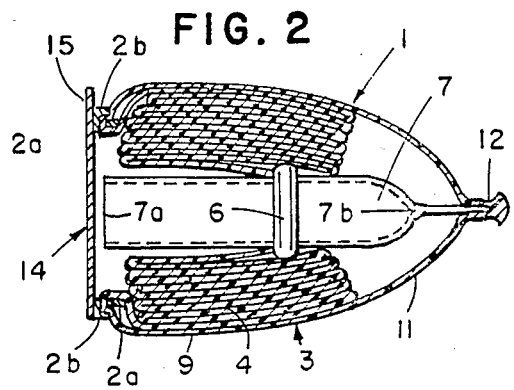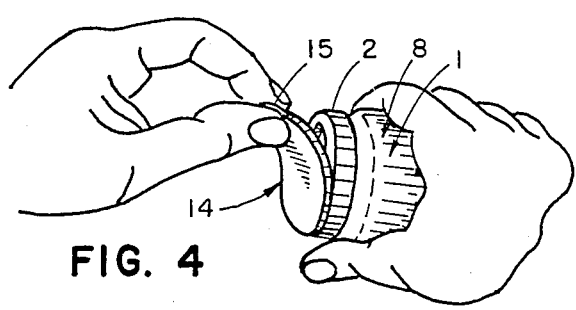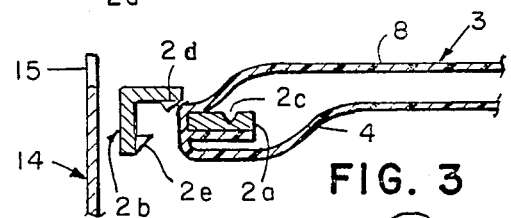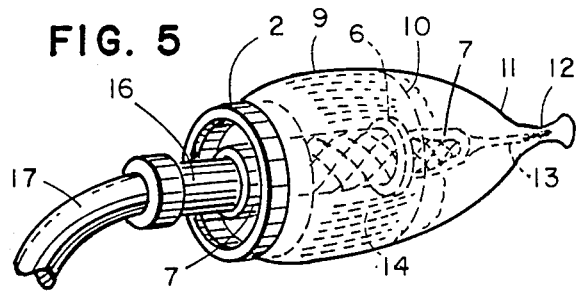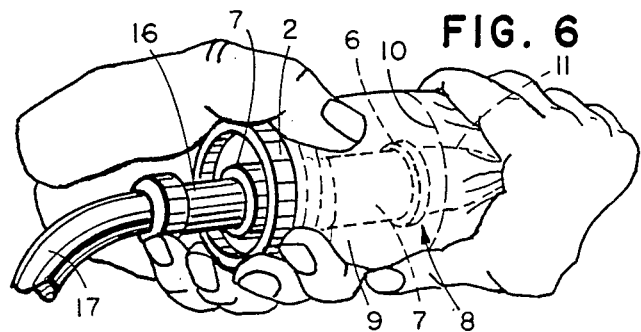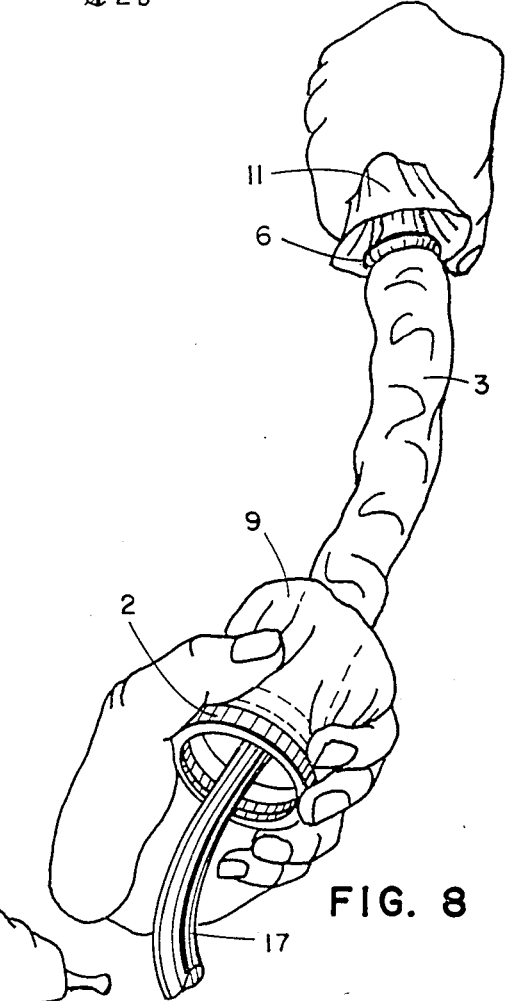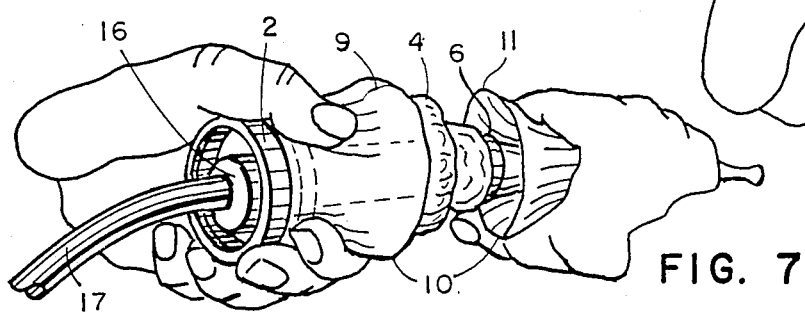

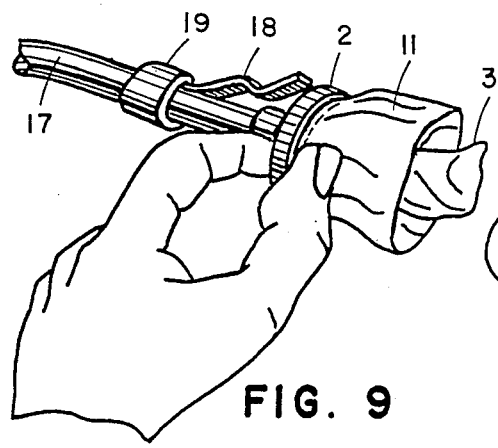
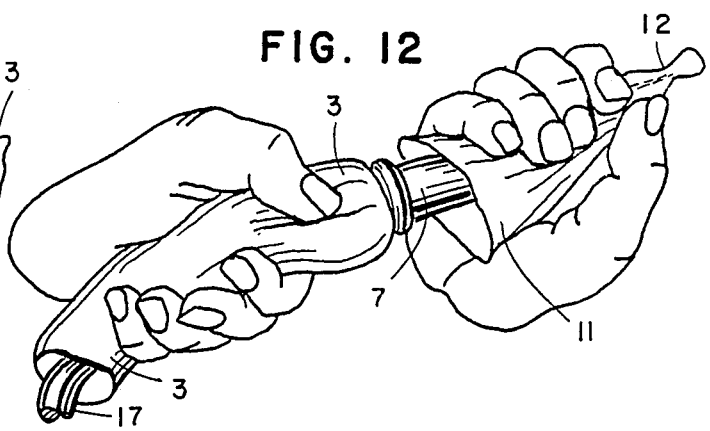
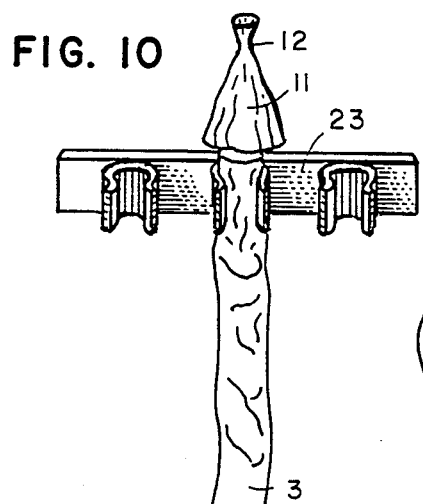
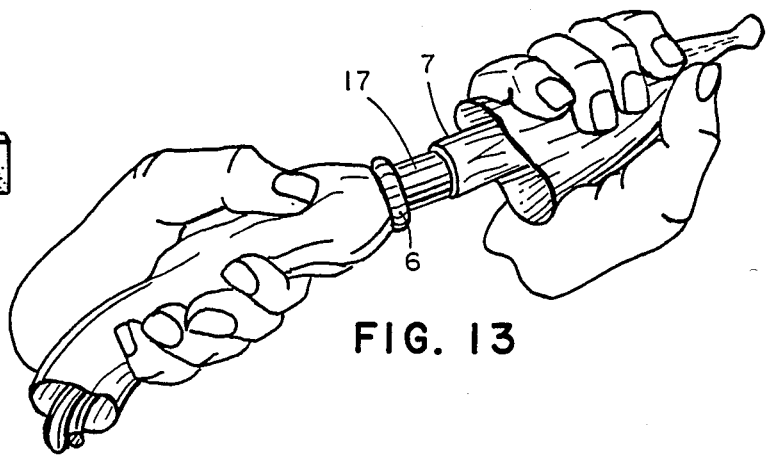
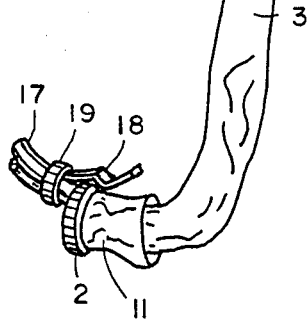
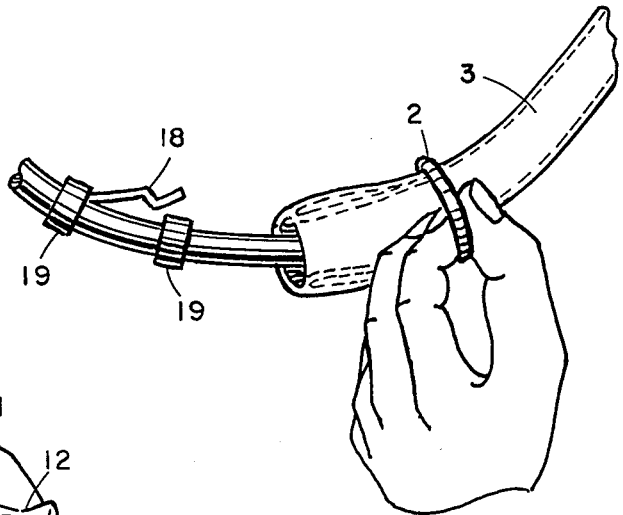
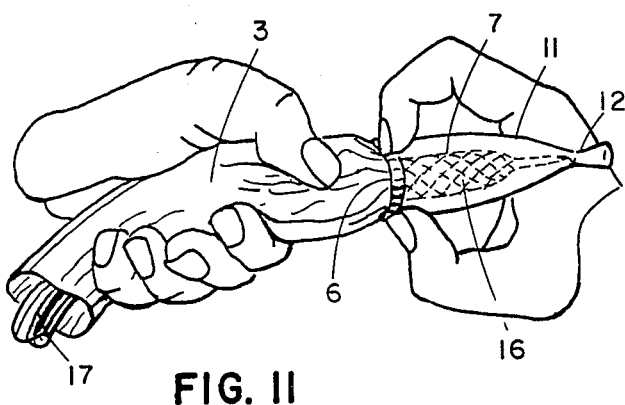

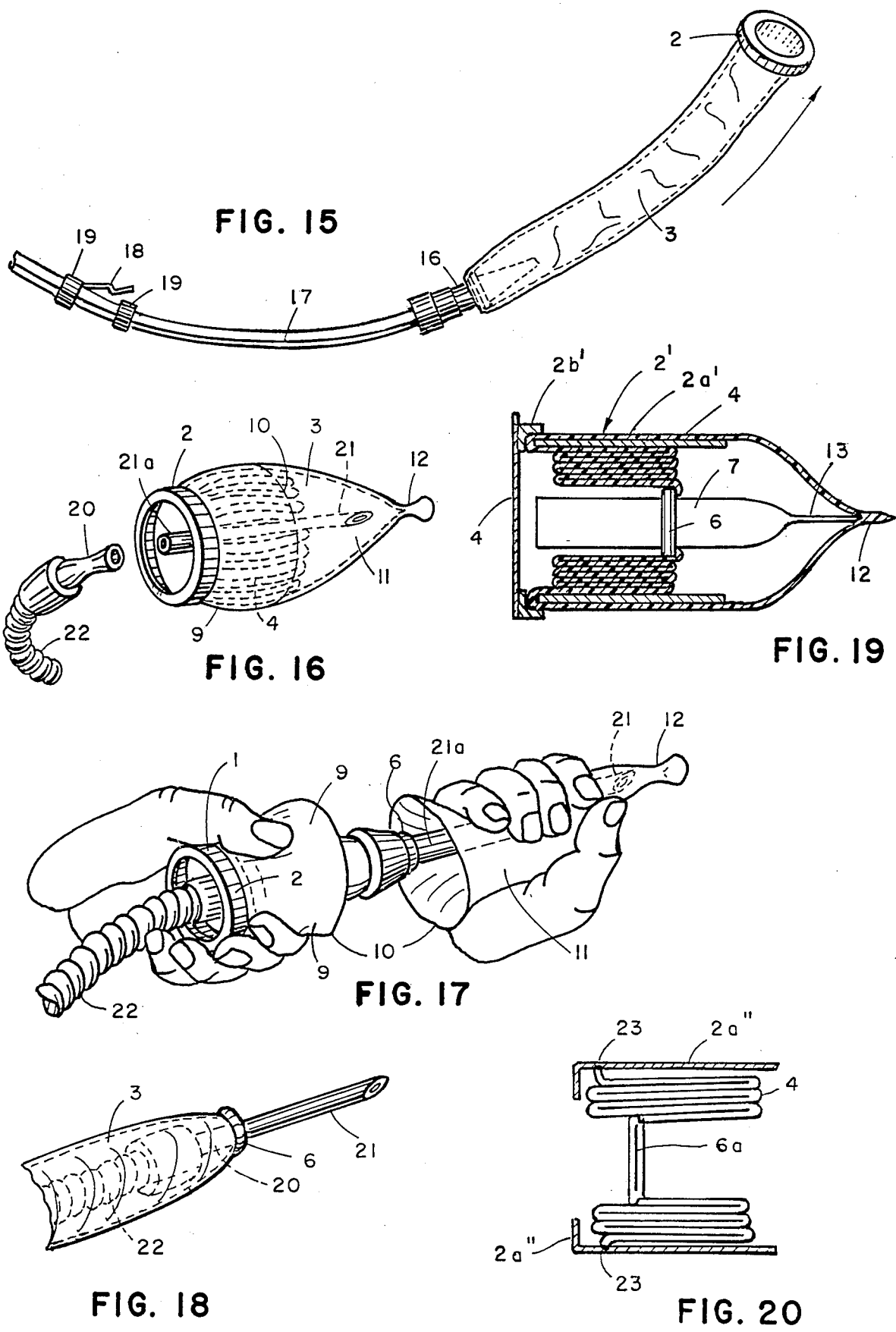

BARRIER FOR DENTAL AND MEDICAL INSTRUMENTS AND APPENDAGES

This invention relates to a device for preventing or at least minimizing the transmission of infectious microorganisms, germs or bacteria which might possibly occur in the use of long appendage type of dental and medical equipment during dental and surgical procedures.

BACKGROUND OF THE INVENTION

There are many types of dental and medical instruments which are connected to or adapted to be connected to relatively long appendages such as air and water hoses, electrical cords, fiber optic cords, and the like. Examples of such instruments are air and water syringes, high and low speed hand piece drillers, ultrasonic sealers, fiber optic wands, ultra-violet or visible curing wands and the like.

With all of these types of instruments, there has been a need for a packaged sanitary drape that can be easily installed on the instrument and its appendage without contaminating the instrument, appendage or outer surface of the drape. The problem has been the cumbersomeness in handling an elongated drape which may be 3 or 4 feet long while placing it on the appendage especially without contaminating the drape with the bacteria from the operator's hands or which may "fall out" from the appendage.

The only drapes known by me for enclosing dental or medical equipment is disclosed in U.S. Pat. Nos. 3,528,720 and 3,698,791. In both of these devices, sack-like envelopes of flexible material are provided for completely enclosing a microscope and its support structure. These two drapes are primarily directed to the specific requirements of a microscope, i.e., the handling of heat generated by the illuminating lamp of the microscope and means for covering the objective lens of the microscope. Both of such prior art devices fail to provide any convenient means for draping the cover over the microscope and its support. Further, neither of such devices provides any concepts for quickly and easily covering an instrument and its appendage such as a flexible hose, cord or the like which is several feet long. Also, although such devices disclose sterile packages, neither of such devices provide a compact packaged drape that is kept sterile and can be easily and quickly manipulated to perform its covering function.

SUMMARY OF THE INVENTION

The cover or drape of the present invention is directed to a sleeve of flexible, very thin, plastic material to which a slip ring is attached at one end. The slip ring is of sufficient diameter so that it can slip or pass over the instrument and its appendage. At the other end of the sleeve is provided a sealing means for sealingly attaching the sleeve to the instrument. Such sealing means can take one of several forms depending upon whether the instrument is disposable. In any form, the entire length of sleeve, which can be several feet long, is folded in an accordion-like fashion.

If the instrument is not disposable, the sealing means may comprise a short tubular member to which the other end of the sleeve is detachably secured by a seal ring, such tubular element being of sufficient inside diameter to receive the non-disposable instrument. In this embodiment, the instrument is inserted through the ring, the accordion folded sleeve and the tubular element, after which the seal ring at the end of the sleeve is detached from the tubular element and then sealingly attached to the instrument.

A plastic seal ring may be molded to produce a thin, stiff, plastic ring which can be of various diameters to fit existing equipment of various sizes. In lieu of a preformed seal ring, the open end of the sleeve may be taped to the instrument after placement, as is commonly done in sterile surgical procedures.

In the embodiment of this invention in which the instrument is disposable, the tubular element is replaced by the instrument to which the other end of the sleeve is sealingly attached such as by a seal ring or an adhesive tape; thus, incorporating the disposable instrument into the package.

Preferably in any of these embodiments, a housing or pouch is formed to completely enclose the package except for the opening to the slip ring. This pouch is preferably formed by a continuation of the sleeve from the circumference of the slip ring, the end of such continuation of the sleeve being sealed. The entire package is enclosed by a detachable disk located over the opening to the slip ring and sealed to the slip ring.

This package provides a device which, as will now be described, is compact, can be made sterile, and is conveniently and easily usable for draping over and covering relatively long lengths of instrument appendages such as hoses and cords to which dental and medical instruments are attached.

BRIEF DESCRIPTION OF THE DRAWINGS

FIG. 1 is a side-elevational, perspective view of the package forming one embodiment of my invention;

FIG. 2 is a side elevational, cross section of the package as disclosed in FIG. 1;

FIG. 3 is an enlarged, cross-sectional view of a portion of the structure of FIGS. 1 and 2 depicting the connection of the slip ring to the sleeve;

FIG. 4 is a side-elevational, perspective view of the package of FIG. 1 illustrating the first step in the use thereof;

FIGS. 5–13, inclusive, are side-elevational, perspective views of the package of FIG. 1 illustrating in sequence the steps for applying the sleeve over a non-disposable instrument and its appendage and attaching the sleeve thereto;

FIGS. 14 and 15 are partial, side-elevational, perspective views of the sleeve and illustrating the removal thereof from the instrument and its appendage;

FIGS. 16, 17 and 18 are side-elevational, perspective views of a second embodiment of this invention disclosing sequential steps in the utilization and application of the present invention to a package in which a disposable instrument is incorporated into the package; and FIG. 19 is a side-elevational, cross-sectional view of a modified embodiment of the invention from that disclosed in FIGS. 1–3.

FIG. 20 is a side elevational, cross-sectional, partial view of another modified embodiment of this invention.

DESCRIPTION OF THE PREFERRED EMBODIMENT

Referring to FIGS. 1, 2 and 3 of the drawings, reference numeral 1 designates the package device of this invention which includes the slip ring 2 formed of two parts 2a and 2b between which is clenched an elongated sleeve 3 comprising an accordion-folded portion 4 and a pouch portion 8. Both the accordion-folded portion 4 and the pouch portion 8 of the sleeve extend in the same direction with the pouch surrounding and completely encompassing the accordion portion 4 as disclosed in both FIGS. 1 and 2. Mounted over the opening of the slip ring 2 is a cover 14 adhered to the ring 2b of the slip ring 2. Mounted inside of the pouch 8 is a support tube 7 to which the extreme end of the folded portion 4 of the sleeve 3 is removably attached to the support tube 7 by means of an elastic band which seals the open end of the accordion portion of the sleeve to the support tube for the reasons as will be explained hereinafter. Extending from the support tube 7 is a ripcord to which the end 12 of the pouch portion 8 of the sleeve is sealed and attached for the purpose as will be disclosed hereinafter.

The sleeve 3 is generally an elongated drape fabricated from a thin, preferably transparent, plastic material of approximately 1 mil (0.001 inches) of thickness. The material can be low density, flexible, low temperature, thermoplastic material, such as polyethylene, or it can be higher density, high temperature, thermoplastic material, such as nylon. As best illustrated in FIG. 2, the accordion-folded portion 4 of the sleeve can be several feet long when unfolded depending upon the length of the object to be covered by the sleeve. The pouch portion 8 of the sleeve need only be several inches long so as to correspond to some extent with the length of the instrument with which the device is to be used. Intermediate the end of the pouch portion 8 is provided a perforated tear line 10 for disconnecting the front portion 11 of the pouch from the rear portion 9 of the pouch. This disconnection or separation of the two portions of the pouch 9 and 11 is essential to permit the extension of the sleeve over the appendages of the instrument as will be described hereinafter.

The sleeve 3 is clenched between the two parts 2a and 2b of the slip ring 2 so that the slip ring 2 is attached securely to the sleeve 3 at the juncture between the pouch 8 and the accordion-folded portion 4 of the sleeve. This is accomplished by configuring the two parts so that one snaps on to the other or by using an adhesive. As disclosed in FIG. 3 the slip ring 2 is formed of two parts 2a and 2b. Part 2a has an indent 2c in its top surface while part 2b has the detents 2d and 2e on each of its legs. Thus, when the part 2b is snapped over the part 2a the detent 2d extends into the indent 2c and the detent 2e hooks around the front edge of the part 2a. This is only one representative way of snap fitting the two parts together over the material of the sleeve 3 so as to secure the slip ring onto the sleeve. The slip ring could be made of just one part and fastened to the sleeve with an adhesive only. It should be understood that within the broadest aspect of this invention, pouch portion 8 of the sleeve and accordion-folded portion 4 of the sleeve could be separate, each being attached separately to the slip ring 2, or the pouch could be loose from the slip ring.

It is important as it will become evident from a description of the operation of this invention that the slip ring has sufficient rigidity so that it can be grasped by the operator. For this purpose, the slip ring may be made of molded paper, plastic or metal, such as metal foil. Further, within a more narrow aspect of this invention, the slip ring can be of a length so as to extend over the accordion-folded portion of the sleeve as disclosed in FIG. 19 at 2a'. In this embodiment, the slip ring covers and protects the accordion-folded sleeve during storage and installation. It is also important that the slip ring be of sufficient diameter so as to easily pass over the cord or other appendage to which the instrument is attached, all as will be described hereinafter.

In the embodiment of FIG. 20, the seal ring and seal ring support are supplanted by a stiff plastic seal ring 6a which eliminates the need for a seal ring tube support. In this embodiment, the slip ring 2a'' is one piece and sufficiently long to cover the accordion-folded sleeve 4 which is adhesively secured to slip ring 2a'' at 23.

Referring back to FIGS. 1–12 and 19, the seal ring support 7 is an elongated tube open at one end 7a and closed at the other end 7b and from which extends the ripcord 13. The extreme end of the folded portion 4 of sleeve 3 is fixed to the seal ring support by an elastic seal ring 6. This elastic seal ring should be sufficiently elastic to remove from the support 7 and cause to clamp on or seal on an instrument inserted into the hollow seal ring support 7. The elastic seal ring can be made of elastic latex-type material which will allow easy passing of the seal ring over large and irregular parts of the instrument and eventually seal over a part of the instrument so as to prevent bacteria from passing between the instrument and the inside of the sleeve.

The ripcord 13 extending from the seal ring support 7 is an elongated member of reduced diameter. It can be an extension of the support 7 or a separate member attached to the support 7. It has to be of sufficient strength so that it can pull out the seal ring support 7 from under the seal ring 6, thereby accurately placing the seal ring on the instrument located in the support 7 without contamination.

The cover 14 for the slip ring 7 can be constructed of many different materials such as an adhesive-backed foil or a paper disc. As previously stated, the cover 14 is adhered to the slip ring 2. It has a tab 15 which extends beyond the periphery of the slip ring 2 permitting the operator to grasp it and peel the cover from the opening.

FIGS. 4 through 10 disclose the application of this invention to existing equipment. Specifically, FIGS. 4–11 and the following description applies the sleeve to a high volume evacuation or suction tip 16 utilized by dentists. However, it should be understood that this invention could be applied to many different types of both dental and medical instruments to which long appendages such as cords and the like are secured and it is desirable to cover at least a portion of the instrument and the appendage. Examples of such instruments are drills, ejection tips, syringes and the like.

The first step in the use of the device is to remove the cover 14. This is accomplished by grasping the tab 15 and pulling the cover or disc 14 off of the slip ring 2 as disclosed is FIG. 4. This exposes the open end 7a of the seal ring support tube 7 permitting the instrument 16 to be inserted therein a disclosed by FIG. 5. Extending from the instrument 16 is the elongated appendage, which is this case is an air hose 17.

With the instrument 16 inserted into the support tube 7 the operator grasps the front and rear portions 9 and 11 of the pouch 8 on each side of the perforated tear line 10 as disclosed in FIG. 6. The two portions of the pouch are pulled in opposite directions causing the pouch to tear along the tear line 10 separating the portions 9 and 11 of the pouch as disclosed in FIG. 7. In grasping the portions of the pouch 11, the operator with one hand grasping the front portion 11 of the pouch 8 must also grasp the ripcord 13 and the front end 7b of the seal ring support tube 7 and also must firmly grasp the inserted instrument through the pouch and seal ring support (which must be flexible at its closed end).

The slip ring 2 is then passed down around the appendage 17, which is this case is an air hose, causing the accordion portion 4 of the sleeve 3 to be unfolded and drawn down around the hose 17 as disclosed in FIG. 8. The sleeve is pulled the entire length of the appendage 17 to a clip 18 which is permanently attached to the hose 17 by tape 19 or other suitable means.

The apparatus thus far can be prepared to this point without cleaning the hands and can be left until just before use by hanging in place on a hand piece holder such as holder 23 (FIG. 10). The position of the seal ring 6 is adjusted in relation to the instrument 16, if necessary, as all disclosed in FIG. 11.

When the instrument is to be used, the sleeve and that portion of the equipment enclosed thereby is grasped with one hand and the front portion of the pouch, the ripcord 13, and the seal ring support 7 are grasped with the other hand as disclosed in FIG. 12. The seal ring support 7 is pulled away from the seal ring 6 which, because of its elasticity, drops onto and grasps the instrument 16 to provide a seal between the instrument and the front end of the sleeve 3. The front end of the pouch, the ripcord 13 and the seal ring support 7 are then discarded. The instrument is then ready to be used by the dentist or doctor, the appendage in the area where the instrument is used being completely covered and sealed so as to prohibit the fall out of bacteria from the cord or appendage 17. Bacteria from the patient is also prevented from accumulating on the cord or appendage 17.

After the equipment has been used, the sleeve is removed by grasping the slip ring 2 and drawing the slip ring out of the ring clip and down the hose as disclosed in FIG. 14. The ring is drawn on the outside of the sleeve 3 which causes the sleeve to be turned inside-out as disclosed in FIGS. 14 and 15. Thus, the outer contaminated surface of the sleeve is completely covered keeping all the bacteria inside the sleeve and thus making the disposal of the sleeve more safe and less hazardous to personnel.

MODIFICATION FOR DRAPING DISPOSABLE INSTRUMENTS

Frequently dentists and doctors use disposable instruments which are used once on a patient and then discarded or thrown away. FIGS. 16, 17 and 18 disclose a modification of this invention adapted for utilizing disposable instruments such as that designated by reference numeral 21 in FIGS. 16, 17 and 18.

In this modification, the structure of the device is substantially the same as described above except the seal ring support 7 is unnecessary since the disposable instrument 21, such as a plastic suction tip or saliva injector, is substituted for the seal ring support 7. In this embodiment, the seal ring 6 is mounted directly on the instrument. The sleeve can also be fixed to the disposable instrument by an adhesive-backed tape.

In the use of the embodiment as disclosed in FIGS. 16, 17, and 18, the steps as depicted in FIGS. 11, 12 and 13 are eliminated since the seal ring is already in place on the instrument.

Briefly describing the application of the modification as disclosed in FIGS. 16, 17 and 18, the cover 14 is removed by pulling on tab 15 in the same way as described above. This exposes the back end 21a of the disposable suction tip 21 making it accessible for connecting the appendage such as the tube 22 to the instrument 21 which in this case is a suction tip. This is accomplished by inserting the suction connector 20 over the end 21a of the suction tip 21.

The front end of the pouch 11 and the suction tip covered thereby is grasped by one hand of the operator and the other hand of the operator grasp the slip ring 2 which is jerked away from the other hand causing the pouch to separate at the perforated tear line as disclosed is FIG. 17. This permits the slip ring 2 to be passed down around the suction hose 22 drawing with it the accordion part 4 of the sleeve 3. The slip ring is pulled to the full length of the tube 22 until it reaches a ring clip like that disclosed in FIG. 9. The slip ring is attached to the clip, the front part of the pouch 11 is discarded and the instrument is ready to be used with the tube 22 near the area in which the instrument is to be used completely enclosed.

After use, the sleeve is removed as disclosed above in relation to FIGS. 14 and 15.

It should be readily evident that this particular device provides for the ease of draping a sleeve over, around and down irregular equipment hoses of dental and medical equipment. This can be accomplished by only one operator as opposed to two people, one who handles the hose and one with sterile hands who applies the draping material. It should be also be evident that this invention permits the easy removal of the sleeve after use. It allows the removal of the sleeve "inside-out" so that the contaminated outer surface is on the inside, greatly decreasing the hazard to personnel during disposal.

The present invention also permits a compact package which can be dropped into a sterile operating tray and stored in position. It can be easily picked up, handled and installed without contamination of the sleeve or the installer's hands and is easily constructed and assembled.

The feature of the elastic seal ring 6 and the seal ring support 7 provides a unique way for sealing the accordion-folded sleeve to either disposal or non-disposable instruments all as described above. The provisions of a pouch with separable portions such as disclosed by the tear line 10 provides for a fast and efficient opening of the pouch with unclean hands but without contamination of the contents since the front portion of the pouch remains in position covering the tip of the equipment as the slip ring is being drawn over the hose and while the back portion of the pouch remains in position covering the accordion folds. Further, it should be understood that if a sterile device is required, the tear line can be replaced by a means which connects the front portion of the pouch with the rear portion without leaving any perforations through which bacteria could pass. Sterile storage could also be obtained by providing a second impervious storage bag in which the entire package is contained.

Having described my invention, it should become evident that many different embodiments and variations of the components as disclosed herein can be made all without departing from the spirit of the invention. Accordingly, my invention is to be limited only as set forth by the language of the appended claims and the equivalents thereof.

The embodiments of the invention in which an exclusive property or privilege is claimed are defined as follows:

1. A device for covering a dental or medical instrument and elongated appendages extending from said dental or medical instruments for the purpose of preventing the contamination of said instruments and appendages extending from said instruments comprising: an elongated sleeve substantially longer than the said instruments with which they are intended to be used and formed from a thin, flexible, impervious material; said sleeve having first and second ends and being collapsible between said ends into a compact package; said sleeve having an opening at said first end; a ring-like element mounted on said first end and folded in accordion-like fashion whereby said instrument can be inserted through said first open end and the center of said accordion-folded sleeve to said second end; of said sleeve around the said opening, said ring-like element being sufficiently rigid to define the periphery of said opening and to permit an operator to grasp the same and pull said ring to expand the accordion-folded sleeve attached thereto over said appendages, and said ring-like element being sufficiently long to cover the accordion-folded portion of said sleeve.

2. The device of claim 1 in which the second end of said sleeve includes an opening for receiving an instrument attached to said appendages; and sealing means at said opening for attaching and sealing said second end of said sleeve to said instrument with said instrument extending through said opening at said second end.

3. A device for covering elongated appendages extending from dental or medical instruments for the purpose of preventing the contamination of said appendages comprising: an elongated sleeve formed from a thin, flexible, impervious material, said sleeve having an opening at one end; a ring-like element mounted on said one end of said sleeve around the said opening, said ring-like element being sufficiently rigid to define the periphery of said opening and to permit an operator to grasp the same and pull said ring and the sleeve attached thereto over said appendages; said sleeve having a substantial portion thereof folded in accordion fashion; and an enclosure means attached to said ring for enclosing said accordion folded sleeve portion to prevent such portion from being exposed to contaminating micro-organisms.

4. The device of claim 3 in which the enclosure means includes a pouch attached to said ring-like element and covering said accordion-folded portion of said sleeve and a cover is removably secured to the ring-like element to cover the opening defined thereby.

5. The device of claim 4 in which means is provided to separate at least a portion of said pouch from said ring-like element whereby the ring-like element with a separated portion of said pouch can be pulled over the appendages independent of the remaining portion of said pouch.

6. The device of claim 4 in which the pouch is a sleeve of flexible, impervious material secured to and extending from said ring-like element over said compacted sleeve and sealed at its end to contain said accordion-folded portion of said sleeve.

7. The device of claim 3 in which means is provided to separate at least a portion of said pouch from said ring-like element whereby the ring-like element with a separated portion of said pouch can be pulled over the appendages independent of the remaining portion of said pouch.

8. The device of claim 3 in which said sleeve has a second end; a disposable instrument provided in an opening at said second end of said sleeve, sealing means at said opening at said second end attaching and sealing said second end of said sleeve to said instrument, said instrument being located inwardly of the accordion-folded portion of said sleeve and contained within said enclosure.

9. The device of claim 8 in which means is provided to separate at least a portion of said pouch from said ring-like element whereby the ring-like element with a separated portion of said pouch can be pulled over the appendages independent of the remaining portion of said pouch.

10. A device for covering elongated appendages extending from dental or medical instruments for the purpose of preventing the contamination of said appendages comprising: an elongated sleeve formed from a thin, flexible, inpervious material, said sleeve having an opening at one end; a ring-like element mounted on said one end of said sleeve around the said opening, said ring-like element being sufficiently rigid to define the periphery of said opening and to permit an operator to grasp the same and pull said ring and the sleeve attached thereto over said appendages; said sleeve including a second end with an opening for receiving an instrument attached to said appendages; and sealing means at said opening for attaching and sealing said second end of said sleeve to said instrument with said instrument extending through said opening at said second end; and a tube provided at said second end of said sleeve, said tube extending into said opening of said second end of said sleeve and adapted to received an elongated dental or medical instrument; said sealing means being adapted to initially attach said second end of said sleeve to said tube and after said instrument is inserted in said tube to sealingly attach said second end of said sleeve to said elongated instrument.

11. The device of claim 10 in which an enclosure means is attached to said ring-like element for enclosing said sleeve and tube to prevent the same from being exposed to contaminating micro-organisms.

12. The device of claim 10 in which a substantial portion of said sleeve is folded in accordion fashion and an enclosure means extends from said ring-like element for enclosing said accordion-folded sleeve portion.

13. The device of claim 12 in which the enclosure means includes a cover removably secured to the ring-like element to cover the opening defined thereby and a pouch is secured to the periphery of said ring-like element and contains said accordion-folded portion of said sleeve.

14. The device of claim 12 in which means is provided to separate at least a portion of said pouch from said ring-like element whereby the ring-like element with a separated portion of said pouch can be pulled over the appendages independent of the remaining portion of said pouch.

15. The device of claim 10 in which the tube is closed at one end, said closed end being connected to the remaining portion of said container means.

16. A device for covering elongated appendages extending from dental or medical instruments for the purpose of preventing the contamination of said appendages comprising: an elongated sleeve formed from a thin, flexible, impervious material, said sleeve having an opening at one end; a ring-like element mounted on said one end of said sleeve around the said opening, said ring-like element being sufficiently rigid to define the periphery of said opening and to permit an operator to grasp the same and pull said ring and the sleeve attached thereto over said appendages; and a clip attached to said appendages, said clip being adapted to removably hold said ring-like element and said sleeve in the extended covered position over said appendages.

17. A device for covering elongated appendages extending from dental or medical instruments for the purpose of preventing the contamination of said appendages comprising: an elongated sleeve having a thin, flexible, impervious material having openings at both ends and folded in accordion fashion into a short, compact part; a ring-like element mounted on one end providing an opening for receiving an instrument and its appendage and a sealing means at the other end of said sleeve for attaching to an instrument in sealing relationship thereto; an enclosure for said sleeve; and means permitting separation of said enclosure whereby the accordion-folded sleeve can be extended by pulling the ring-like element away from the sealing means to drape the sleeve over said appendage.

18. The device of claim 17 in which a tube is provided at said other end of said sleeve, said tube extending into said opening of said other end of said sleeve and adapted to receive an elongated dental or medical instrument; said sealing means being adapted to initially attach said other end of said sleeve to said tube and after said instrument is inserted in said tube to sealingly attach said other end of said sleeve to said elongated instrument.

* * * * *

UNITED STATES PATENT AND TRADEMARK OFFICE
CERTIFICATE OF CORRECTION

PATENT NO. : 4,723,912
DATED : February 9, 1988
INVENTOR(S) : Dick Nieusma

It is certified that error appears in the above-identified patent and that said Letters Patent is hereby corrected as shown below:

Column 7, claim 1, line 9;

After "first end" and before ";" insert --and folded in accordian like fashion whereby said instrument can be inserted through said first open end and the center of said accordian folded sleeve to said second end--.

Column 7, claim 1, line 10;

After "first end" delete "and folded in accordian like fashion whereby said instrument can be inserted through said first open end and the center of said accordian folded sleeve to said second end".

Column 8, claim 10, line 29;

"received" ahould be --receive--.

Signed and Sealed this
Sixteenth Day of August, 1988

*Attest:*

DONALD J. QUIGG

*Attesting Officer*    *Commissioner of Patents and Trademarks*